(12) United States Patent
Shennib

(10) Patent No.: US 9,894,450 B2
(45) Date of Patent: *Feb. 13, 2018

(54) SELF-FITTING OF A HEARING DEVICE

(71) Applicant: IHEAR MEDICAL, INC., San Leandro, CA (US)

(72) Inventor: Adnan Shennib, Oakland, CA (US)

(73) Assignee: IHEAR MEDICAL, INC., San Leandro, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/357,942

(22) Filed: Nov. 21, 2016

(65) Prior Publication Data

US 2017/0070833 A1 Mar. 9, 2017

Related U.S. Application Data

(63) Continuation of application No. 14/683,946, filed on Apr. 10, 2015, now Pat. No. 9,532,152, which is a
(Continued)

(51) Int. Cl.
*H04R 25/00* (2006.01)
*A61B 5/12* (2006.01)
*A61B 5/00* (2006.01)

(52) U.S. Cl.
CPC ............ *H04R 25/70* (2013.01); *A61B 5/123* (2013.01); *H04R 25/50* (2013.01); *A61B 5/7475* (2013.01); *H04R 25/305* (2013.01); *H04R 25/505* (2013.01)

(58) Field of Classification Search
USPC .......................................... 381/56
See application file for complete search history.

(56) References Cited

U.S. PATENT DOCUMENTS

| 4,759,070 A | 7/1988 | Voroba |
| 5,197,332 A | 3/1993 | Shennib |

(Continued)

FOREIGN PATENT DOCUMENTS

| JP | 57188235 A | 11/1982 |
| JP | 06105828 A | 4/1994 |

(Continued)

OTHER PUBLICATIONS

First OA received in JP Application No. 2016-526995, dated Jan. 24, 2017.
(Continued)

*Primary Examiner* — Amir Etesam
(74) *Attorney, Agent, or Firm* — Dorsey & Whitney LLP

(57) ABSTRACT

Disclosed herein are systems and methods enabling hearing aid fitting by a non-expert consumer at home. The method in one embodiment involves delivering a sequence of test audio signals corresponding to natural sound segments to a non-acoustic input of a programmable hearing device in-situ, while allowing the consumer to adjust fitting parameters based perceptual assessment of hearing device output. The sound segments define a fitting soundscape representing a practical range of sounds within the normal human auditory range, with each sound segment corresponding to one or more fitting parameters of the programmable hearing device. The consumer is instructed to listen to the output of the in-situ hearing device and adjust controls related to corresponding fitting parameters. In one embodiment, the fitting system comprises a personal computer and a handheld device providing calibrated test audio signals and a programming interface. The systems and methods disclosed herein allow home dispensing of hearing devices without requiring specialized instruments or clinical settings.

8 Claims, 12 Drawing Sheets

Related U.S. Application Data continuation of application No. 14/011,604, filed on Aug. 27, 2013, now Pat. No. 9,031,247.

(60) Provisional application No. 61/847,007, filed on Jul. 16, 2013.

(56) References Cited

U.S. PATENT DOCUMENTS

| | | |
|---|---|---|
| 5,327,500 A | 7/1994 | Campbell |
| 5,553,152 A | 9/1996 | Newton |
| 5,645,074 A | 7/1997 | Shennib et al. |
| 5,659,621 A | 8/1997 | Newton |
| 5,701,348 A | 12/1997 | Shennib et al. |
| 5,785,661 A | 7/1998 | Shennib et al. |
| 5,928,160 A | 7/1999 | Clark et al. |
| 6,137,889 A | 10/2000 | Shennib et al. |
| 6,212,283 B1 | 4/2001 | Fletcher et al. |
| 6,319,207 B1 | 11/2001 | Naidoo |
| 6,359,993 B2 | 3/2002 | Brimhall |
| 6,367,578 B1 | 4/2002 | Shoemaker |
| 6,379,314 B1 | 4/2002 | Horn |
| 6,382,346 B2 | 5/2002 | Brimhall et al. |
| 6,428,485 B1 | 8/2002 | Rho |
| 6,447,461 B1 | 9/2002 | Eldon |
| 6,473,513 B1 | 10/2002 | Shennib et al. |
| 6,522,988 B1 | 2/2003 | Hou |
| 6,546,108 B1 | 4/2003 | Shennib et al. |
| 6,674,862 B1 | 1/2004 | Magilen |
| 6,724,902 B1 | 4/2004 | Shennib et al. |
| 6,840,908 B2 | 1/2005 | Edwards et al. |
| 6,937,735 B2 | 8/2005 | DeRoo et al. |
| 6,940,988 B1 | 9/2005 | Shennib et al. |
| 6,978,155 B2 | 12/2005 | Berg |
| 7,010,137 B1 | 3/2006 | Leedom et al. |
| 7,016,511 B1 | 3/2006 | Shennib |
| 7,037,274 B2 | 5/2006 | Thoraton et al. |
| 7,113,611 B2 | 9/2006 | Leedom et al. |
| 7,215,789 B2 | 5/2007 | Shennib et al. |
| 7,260,232 B2 | 8/2007 | Shennib |
| 7,298,857 B2 | 11/2007 | Shennib et al. |
| 7,310,426 B2 | 12/2007 | Shennib et al. |
| 7,321,663 B2 | 1/2008 | Olsen |
| 7,362,875 B2 | 4/2008 | Saxton et al. |
| 7,403,629 B1 | 7/2008 | Aceti et al. |
| 7,424,123 B2 | 9/2008 | Shennib et al. |
| 7,424,124 B2 | 9/2008 | Shennib et al. |
| 7,580,537 B2 | 8/2009 | Urso et al. |
| 7,664,282 B2 | 2/2010 | Urso et al. |
| 7,854,704 B2 | 12/2010 | Givens et al. |
| 7,913,696 B2 | 3/2011 | Purcell et al. |
| 7,945,065 B2 | 5/2011 | Menzl et al. |
| 8,073,170 B2 | 12/2011 | Kondo et al. |
| 8,077,890 B2 | 12/2011 | Schumaier |
| 8,155,361 B2 | 4/2012 | Schindler |
| 8,184,842 B2 | 5/2012 | Howard et al. |
| 8,243,972 B2 | 8/2012 | Latzel |
| 8,284,968 B2 | 10/2012 | Schumaier |
| 8,287,462 B2 | 10/2012 | Givens et al. |
| 8,379,871 B2 | 2/2013 | Michael et al. |
| 8,396,237 B2 | 3/2013 | Schumaier |
| 8,447,042 B2 | 5/2013 | Gurin |
| 8,467,556 B2 | 6/2013 | Shennib et al. |
| 8,503,703 B2 | 8/2013 | Eaton et al. |
| 8,571,247 B1 | 10/2013 | Oezer |
| 8,718,306 B2 | 5/2014 | Gommel et al. |
| 8,798,301 B2 | 8/2014 | Shennib |
| 8,855,345 B2 | 10/2014 | Shennib et al. |
| 9,031,247 B2 | 5/2015 | Shennib |
| 9,060,233 B2 | 6/2015 | Shennib et al. |
| 9,078,075 B2 | 7/2015 | Shennib et al. |
| 9,107,016 B2 | 8/2015 | Shennib |
| 9,253,583 B2 | 2/2016 | Blamey et al. |
| 9,326,706 B2 | 5/2016 | Shennib |
| 9,439,008 B2 | 9/2016 | Shennib |
| 9,532,152 B2 | 12/2016 | Shennib et al. |
| 2001/0008560 A1 | 7/2001 | Stonikas et al. |
| 2001/0009019 A1 | 7/2001 | Armitage |
| 2001/0051775 A1 | 12/2001 | Rho |
| 2002/0027996 A1 | 3/2002 | Leedom et al. |
| 2002/0085728 A1 | 7/2002 | Shennib et al. |
| 2003/0007647 A1 | 1/2003 | Nielsen et al. |
| 2003/0078515 A1 | 4/2003 | Menzel et al. |
| 2004/0028250 A1 | 2/2004 | Shim |
| 2004/0073136 A1 | 4/2004 | Thornton et al. |
| 2004/0122873 A1 | 6/2004 | Wright, Jr. et al. |
| 2004/0165742 A1 | 8/2004 | Shennib et al. |
| 2005/0094822 A1* | 5/2005 | Swartz .............. A61B 5/121 381/56 |
| 2005/0226447 A1 | 10/2005 | Miller, III |
| 2005/0245991 A1 | 11/2005 | Faltys et al. |
| 2005/0249370 A1 | 11/2005 | Shennib et al. |
| 2005/0259840 A1 | 11/2005 | Gable et al. |
| 2005/0283263 A1 | 12/2005 | Eaton et al. |
| 2006/0094981 A1 | 5/2006 | Camp |
| 2006/0210104 A1 | 9/2006 | Shennib et al. |
| 2006/0291683 A1 | 12/2006 | Urso et al. |
| 2007/0009126 A1 | 1/2007 | Fischer et al. |
| 2007/0071265 A1 | 3/2007 | Leedom et al. |
| 2007/0076909 A1 | 4/2007 | Roeck et al. |
| 2007/0189545 A1 | 8/2007 | Geiger et al. |
| 2007/0237346 A1 | 10/2007 | Fichtl et al. |
| 2008/0240452 A1 | 10/2008 | Burrows et al. |
| 2008/0273726 A1 | 11/2008 | Yoo et al. |
| 2008/0298600 A1 | 12/2008 | Poe et al. |
| 2009/0220099 A1* | 9/2009 | Voix .............. A61F 11/08 381/59 |
| 2010/0040250 A1 | 2/2010 | Gebert |
| 2010/0119094 A1 | 5/2010 | Sjursen et al. |
| 2010/0145411 A1 | 6/2010 | Spitzer |
| 2010/0191143 A1 | 7/2010 | Ganter |
| 2010/0226520 A1 | 9/2010 | Feeley et al. |
| 2010/0239112 A1 | 9/2010 | Howard et al. |
| 2010/0268115 A1 | 10/2010 | Wasden et al. |
| 2010/0284556 A1 | 11/2010 | Young |
| 2010/0290654 A1 | 11/2010 | Wiggins et al. |
| 2011/0058697 A1 | 3/2011 | Shennib et al. |
| 2011/0176686 A1 | 7/2011 | Zaccaria |
| 2011/0188689 A1 | 8/2011 | Beck et al. |
| 2011/0190658 A1 | 8/2011 | Sohn et al. |
| 2011/0200216 A1 | 8/2011 | Lee et al. |
| 2011/0206225 A1 | 8/2011 | Møller et al. |
| 2012/0051569 A1 | 3/2012 | Blamey et al. |
| 2012/0095528 A1 | 4/2012 | Miller, III et al. |
| 2012/0130271 A1 | 5/2012 | Margolis et al. |
| 2012/0157876 A1 | 6/2012 | Bang et al. |
| 2012/0177212 A1 | 7/2012 | Hou et al. |
| 2012/0177235 A1 | 7/2012 | Solum |
| 2012/0183164 A1 | 7/2012 | Foo et al. |
| 2012/0183165 A1 | 7/2012 | Foo et al. |
| 2012/0189140 A1 | 7/2012 | Hughes |
| 2012/0213393 A1 | 8/2012 | Foo et al. |
| 2012/0215532 A1 | 8/2012 | Foo et al. |
| 2012/0285470 A9 | 11/2012 | Sather et al. |
| 2012/0302859 A1 | 11/2012 | Keefe |
| 2013/0010406 A1 | 1/2013 | Stanley |
| 2013/0177188 A1 | 7/2013 | Apfel et al. |
| 2013/0182877 A1 | 7/2013 | Angst et al. |
| 2013/0223666 A1 | 8/2013 | Michel et al. |
| 2013/0243209 A1 | 9/2013 | Zurbruegg et al. |
| 2013/0243227 A1 | 9/2013 | Kinsbergen et al. |
| 2013/0243229 A1 | 9/2013 | Shennib et al. |
| 2013/0294631 A1 | 11/2013 | Shennib et al. |
| 2014/0003639 A1 | 1/2014 | Shennib et al. |
| 2014/0150234 A1 | 6/2014 | Shennib et al. |
| 2014/0153761 A1 | 6/2014 | Shennib et al. |
| 2014/0153762 A1 | 6/2014 | Shennib et al. |
| 2014/0193008 A1 | 7/2014 | Zukic |
| 2014/0254843 A1 | 9/2014 | Shennib |
| 2014/0254844 A1 | 9/2014 | Shennib |
| 2015/0023512 A1 | 1/2015 | Shennib |
| 2015/0023534 A1 | 1/2015 | Shennib |
| 2015/0023535 A1 | 1/2015 | Shennib |
| 2015/0025413 A1 | 1/2015 | Shennib |
| 2015/0215714 A1 | 7/2015 | Shennib |

(56) References Cited

U.S. PATENT DOCUMENTS

| | | |
|---|---|---|
| 2015/0256942 A1 | 9/2015 | Kinsbergen et al. |
| 2016/0066822 A1 | 3/2016 | Shennib et al. |
| 2016/0080872 A1 | 3/2016 | Shennib et al. |
| 2016/0166181 A1 | 6/2016 | Shennib |
| 2016/0198271 A1 | 7/2016 | Shennib |
| 2016/0337770 A1 | 11/2016 | Shennib |

FOREIGN PATENT DOCUMENTS

| | | |
|---|---|---|
| JP | H10126895 A | 5/1998 |
| JP | 2002191581 A | 7/2002 |
| JP | 2002259714 A | 9/2002 |
| JP | 2005168856 A | 6/2005 |
| JP | 2005286876 A | 10/2005 |
| JP | 2007028609 A | 2/2007 |
| JP | 2008109594 A | 5/2008 |
| KR | 1020050114861 A | 12/2005 |
| KR | 100955033 B1 | 4/2010 |
| KR | 1020100042370 A | 4/2010 |
| WO | 99/07182 A2 | 2/1999 |
| WO | 2006136174 A2 | 12/2006 |
| WO | 2010/091480 A1 | 8/2010 |
| WO | 2011128462 A2 | 10/2011 |
| WO | 2015009559 A1 | 1/2015 |
| WO | 2015009561 A1 | 1/2015 |
| WO | 2015009564 A1 | 1/2015 |
| WO | 2015009569 A1 | 1/2015 |
| WO | 2016044178 A1 | 3/2016 |

OTHER PUBLICATIONS

Extended European Search Report, Extended European Search Report received for EP Appl. 14826999.6 dated Feb. 10, 2017.
U.S. Appl. No. 15/368,342, filed Dec. 2, 2016.
Internet Archive, World Health Organization website "Grades of Hearing Impairment". Retrieved from <https://web.archive.org/web/20121024120107/http://www.who.int/pbd/deafness/hearing_impairment_grades/en> on Aug. 27, 2015.
"Basic Guide to in Ear Canalphones", Internet Archive, Head-Fi.org, Jul. 1, 2012. Retrieved from http://web.archive.org/web/20120701013243/http:www.head-fi.org/a/basic-guide-to-in-ear-canalphones> on Apr. 14, 2015.
"DB HL—Sensitivity to Sound—Clinical Audiograms", Internet Archive, AuditoryNeuroscience.com, Apr. 20, 2013. Retrieved from <https://web.archive.org/web/20130420060438/http://www.auditoryneuroschience.com/acoustics/clinical_audiograms> on Apr. 14, 2015.
"International Search Report and Written Opinion for PCT/US2014/046323 dated Oct. 10, 2014".
"Lyric User Guide", http://www.phonak.com/content/dam/phonak/b2b/C_M_tools/Hearing_Instruments/Lyric/documents/02-gb/Userguide_Lyric_V8_GB_FINAL_WEB.pdf, Jul. 2010.
"Methods for Calculation of the Speech Intelligibility Index", American National Standards Institute, Jun. 6, 1997.
"Specification for Audiometers", American National Standards Institute, Nov. 2, 2010.
"The Audiogram", Internet Archive, ASHA.org, Jun. 21, 2012, Retrieved from <https:/web.archive.org/web/20120621202942/http://www.asha.org/public/hearing/Audiogram> on Apr. 14, 2015.
"User Manual—2011", AMP Personal Audio Amplifiers.
Abrams, , "A Patient-adjusted Fine-tuning Approach for Optimizing the Hearing Aid Response", The Hearing Review, Mar. 24, 2011, 1-8.
Amlani, et al., "Methods and Applications of the Audibility Index in Hearing Aid Selection and Fitting", Trends in Amplication 6.3 (2002) 81. Retrieved from <https://www.ncbi.nlm.nih.gov/pmc/articles/PMC4168961/> on Apr. 14, 2015.
Asha, "Type, Degree, and Configuration of Hearing Loss", American Speech-Language-Hearing Association; Audiology Information Series, May 2011, 1-2.
Convery, et al., "A Self-Fitting Hearing Aid: Need and Concept", http://tia.sagepubl.com, Dec. 4, 2011, 1-10.
Franks, "Hearing Measurements", National Institute for Occupational Safety and Health, Jun. 2006, 183-232.
Kiessling, "Hearing aid fitting procedures—state-of-the-art and current issues", Scandinavian Audiology vol. 30, Suppl 52, 2001, 57-59.
Kryter, "Methods for the calculation and use of the articulation index", The Journal of the Acoustical Society of America 34.11 (1962): 1689-1697. Retrieved from <http://dx.doi.org/10.1121/1.1909094> on Aug. 27, 2015.
Nhanes, "Audiometry Procedures Manual", National Health and Nutrition Examination Survey, Jan. 2003, 1-105.
Sindhusake, et al., "Validation of self-reported hearing loss. The Blue Mountains hearing study", International Journal of Epidemiology 30.6 (2001): 1371-1378. Retrieved from <http://ije.oxfordjournals.org/content/30/6/1371.full> on Aug. 27, 2015.
Traynor, "Prescriptive Procedures", www.rehab.research.va.gov/mono/ear/traynor.htm, Jan. 1999, 1-16.
World Health Organization, "Deafness and Hearing Loss", www.who.int/mediacentre/factsheets/fs300/en/index.html, Feb. 2013, 1-5.
Second Office Action for JP Application No. 2016-526995, dated Aug. 1, 2017.
Ishikawa, et al.; "Cosmetology seeing from the standpoint of aesthetic science—aesthetics and amenity", Fragrance Journal vol. 20 No. 7, Japan, Jul. 1992, pp. 62-70.
Maeda, et al., "The Seasonal Features of Soundscape—Statistical Analysis of the Acoustical Environment of Daily Life Shown in the World of Haiku Using Hayashi's Quantification Theory", Kyushu Institute of Design—The Acoustical Society of Japan research presentation meeting lecture collected papers Autumn I, Japan, corporation Acoustical Society of Japan, Oct. 1992, p. 591-592.
Communication pursuant to Article 94(3) EPC for EP Application No. 14826999.6, dated Nov. 9, 2017.

* cited by examiner

SELF-FITTING OF A HEARING DEVICE

CROSS-REFERENCE TO RELATED APPLICATIONS

This application in a continuation of U.S. Non-Provisional application Ser. No. 14/683,946, entitled "SELF-FITTING OF A HEARING DEVICE", filed Apr. 10, 2015, which is a continuation of U.S. Non-Provisional application Ser. No. 14/011,604, entitled "HEARING AID FITTING SYSTEMS AND METHODS USING SOUND SEGMENTS REPRESENTING RELEVANT SOUNDSCAPE," filed Aug. 27, 2013, issued as U.S. Pat. No. 9,031,247 on Jan. 22, 2015, which claimed the benefit under 35 U.S.C. 119 of the earlier filing date of U.S. Provisional Application 61/847,007 entitled "METHOD OF HEARING AID FITTING USING AUDIO SEGMENTS WITHIN RELEVANT HUMAN SOUNDSCAPE," filed Jul. 16, 2013. The aforementioned provisional and non-provisional applications are hereby incorporated by reference in their entirety, for any purpose.

TECHNICAL FIELD

Examples described herein relate to methods and systems of hearing aid fitting, particularly for administration by a non-expert, including self-fitting by a consumer. This application is related to U.S. Pat. No. 8,467,556, titled, "CANAL HEARING DEVICE DISPOSABLE BATTERY MODULE," U.S. Pat. No. 8,855,345, titled, "BATTERY MODULE FOR PERPENDICULAR DOCKING INTO A CANAL HEARING DEVICE," U.S. Pat. No. 9,326,706 titled "HEARING PROFILE TEST SYSTEM AND METHOD," U.S. Pat. No. 9,107,016 titled, "INTERACTIVE HEARING AID FITTING SYSTEM AND METHODS," and U.S. Pat. No. 9,439,008 titled, "ONLINE HEARING AID FITTING SYSTEM AND METHODS FOR NON-EXPERT USER;" all of which are incorporated herein by reference in their entirety for any purpose.

BACKGROUND

Current hearing aid fitting methods and instrumentations are generally costly and too complex for use by consumers and non-expert operators. The methods generally require administration by a hearing professional in a clinical setting. For example an audiometer is typically required to produce an audiogram report, which forms the basis of hearing assessment and prescriptions in conventional fitting methods. Other instruments used may include a hearing aid analyzer, and a real-ear measurement (REM) instrument. A specialized sound-proof room, sometimes referred to as a sound room, is also generally required for conducting part or all of the fitting process. The fitting prescription from an audiogram report may be determined from a generic fitting formula, such as NAL or POGO, or from a proprietary formula, generally provided by the manufacturer of the hearing aid being fitted. The computations for the prescription are generally limited to hearing professional use, and the resultant prescriptions may vary considerably depending on the formula used, sometimes by as much as 20 decibels due to various factors including personal preferences.

Characterization and verification of a hearing aid prescription are generally conducted by presenting test sounds to the microphone of the hearing device, referred to herein generally as a microphonic or acoustic input. The hearing aid may be worn in the ear during the fitting process, for what is referred to as "real ear" measurements. Or it may be placed in a test chamber for characterization by a hearing aid analyzer. The stimulus used for testing is typically tonal sound but may be a speech spectrum noise or other speech-like signal such as "digital speech." Natural or real-life sounds are generally not employed in determination of a hearing aid prescription. Hearing aid users are generally asked to return to the clinic following real-life listening experiences to make the necessary adjustments. If real-life sounds are used in a clinical setting, a calibration procedure involving probe tube measurements with REM instruments is generally required. Regardless of the particular method used, conventional fittings generally require clinical settings to employ specialized instruments for administration by trained hearing professionals. The term "hearing aid," used herein, refers to all types of hearing enhancement devices, including medical devices prescribed for the hearing impaired, and personal sound amplification products (PSAP) generally not requiring a prescription or a medical waiver. The device type or "style" may be any of invisible in the canal (IIC), in-the-canal (ITC), in the ear (ITE), a receiver in the canal (RIC), or behind the ear (BTE). A canal hearing device refers herein to any device partially or fully inserted in the ear canal.

Programmable hearing aids generally rely on adjustments of the electroacoustic settings programmed within, referred to herein generally as "fitting parameters". Similar to hearing assessments and hearing aid prescriptions, the programming of a hearing aid generally requires specialized programming instruments and the intervention of a hearing professional to deal with complexities related to fitting parameters and programming thereof, particularly for an advanced programmable hearing aid, which may comprise over 15 adjustable parameters, and in some cases over 50 parameters.

For the aforementioned reasons among others, the fitting process for a programmable hearing device is generally not self-administered by the consumer. Instead, a licensed dispensing professional is typically involved for conducting at least one part of the fitting process, which may include hearing evaluation, hearing aid recommendation and selection, fitting prescription, fitting parameter adjustments and programming into the hearing device. This process often requires multiple visits to a dispensing office to incorporate the user's subjective listening experience after the initial fitting. Conventional fitting processes are generally too technical and cumbersome for self-administration, or for administration by a non-expert person. As a result, the cost of a professionally dispensed hearing aid, including clinician effort and the specialized instruments used in clinical settings, can easily reach thousands of dollars, and that cost is almost double for a pair of hearing aids. The high cost of hearing devices thus remains a major barrier preventing many potential consumers from acquiring a hearing aid, which typically costs under $100 to manufacture.

SUMMARY

Disclosed herein are example systems and methods for hearing aid fitting by a non-expert person without resorting to clinical settings and particularly suited for self-fitting by a hearing impaired consumer. The method includes delivering a sequence of calibrated test audio signals, corresponding to multiple suprathreshold test sound segments, directly to an input of a programmable hearing aid in-situ and allowing the consumer to adjust hearing aid parameters based on perceptual assessment. In some embodiments, the test sound segments are obtained from natural sound recordings such as speech and environmental sounds, with each test sound segment comprising a unique combination of sound level and frequency characteristics. The sound segments define a "fitting soundscape" representing a practical range of sounds within the normal human auditory range, with each sound segment corresponding to one or more fitting parameters of the programmable hearing aid. The sound segments are selected to expose the programmable hearing aid to the dynamic and frequency ranges of sound in order to tune the fitting parameters by the subjective response of the consumer, thus eliminating objective assessments and the clinical instrumentations associated thereto used in conventional hearing aid fitting. In some embodiments, the test sound segments include a relatively low level sound, a relatively loud sound, a relatively low frequency sound, a relatively high frequency sound, of which at least two are speech segments, and an environmental sound. The test audio signals are generally produced from digital audio files, and collectively define the "fitting soundscape," relevant for hearing aid parameters, and within the broader "human auditory soundscape". The fitting soundscape essentially represents the range of sound amplitudes and frequencies experienced by an individual in normal daily listening situations. In one embodiment, the test sound levels are at least 20 dB above the threshold of normal (unimpaired) hearing.

The fitting method disclosed herein generally involves instructing the heating aid consumer to listen to the output of the programmable hearing device in-situ, while presenting calibrated test audio signals representing natural sounds to an input of the hearing aid. The consumer may be offered controls to adjust hearing aid parameters using consumer friendly controls with familiar and generally non-technical terms such as volume, loudness, audibility, clarity, etc.

In one embodiment, the fitting system includes a computing system (e.g. a personal computer), a handheld device in communication with the computing device, and a fitting software application executed by the fitting system. The handheld device includes an audio generator configured to deliver test audio signals to the non-acoustic input of the hearing device in-situ. The handheld device may also include a programming interface configured to deliver programming signals to the programmable hearing device in-situ. The handheld device may be provided with USB or other connectivity for interfacing with a broad range of personal computing devices, including for example smartphones and tablet computers.

Systems and methods disclosed herein may be implemented to allow consumers to interactively develop their own "prescription" and program it into their own programmable hearing devices, using perceptual assessment and corresponding controls, without dealing with prescriptive formulae, specialized fitting instruments, and visits to clinical settings. The test audio signals are automatically presented by the disclosed fitting system at predetermined levels to the input of the heating device, preferably electrically or wirelessly, thus eliminating calibration processes associated with sound delivery to the microphone of a hearing aid. Similarly, a programming signal for adjusting hearing aid parameters by the fitting system may be presented electrically or wirelessly at an output of a programming circuit housed within the handheld device.

Examples of fitting systems disclosed herein allow the consumer to interactively manipulate hearing aid parameters based on the perceptual assessment of hearing aid output with test sound segments presented as test audio signals to hearing aid input. The process is repeated for each test segment until all corresponding fitting parameters are adjusted according to the personal preference of the consumer, or best options available according to instructions presented thereto. In some embodiments, the test audio segments are selected with minimal overlap in amplitude and frequency characteristics, thus minimizing the overlap in parameter optimization, and expediting the fitting process for a non-expert user.

In one aspect of the fitting system and method thereof, the consumer may administer the fitting at a reasonably quiet environment, such as in a home or office. This "home fitting" aspect substantially reduces the cost of hearing aid acquisition and eliminates the hassles and inconvenience associated with multiple visits to a professional dispenser setting. In one embodiment, the fitting process is web-based, with a fitting software application hosted by a remote server and executed by a computing system (e.g. personal computer) at the consumer side, in communication with the remote server.

BRIEF DESCRIPTION OF THE DRAWINGS

The above objectives, features, aspects and attendant advantages of the present invention will become apparent from the following detailed description of various embodiments, including the best mode presently contemplated of practicing the invention, when taken in conjunction with the accompanying drawings, in which.

DETAILED DESCRIPTION

Certain details are set forth below to provide a sufficient understanding of embodiments of the invention. Some embodiments, however, may not include all details described herein. In some instances, some well-known structures may not be shown, in order to avoid unnecessarily obscuring the described embodiments of the invention.

Figure 1:
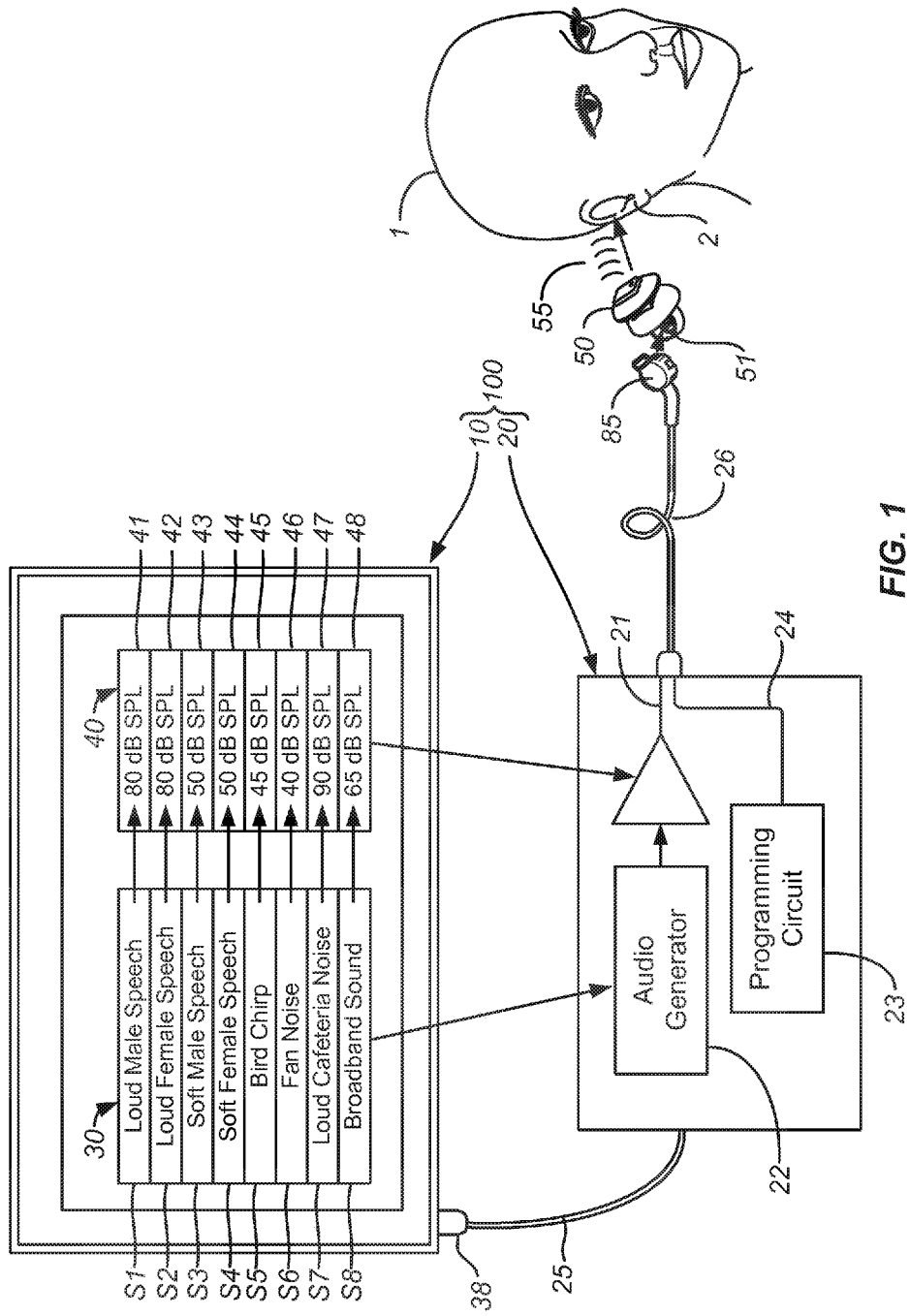
FIG. 1 is a block diagram view of an example hearing aid fitting system, including an audio signal generator, programming interface, sound segments, and programmable hearing device with direct audio input interface, according to one embodiment.

The present disclosure describes example systems and methods, as shown in FIGS. 1-12, for hearing aid fitting by a non-expert consumer without resorting to clinical settings, and particularly suited for self-fitting by a hearing aid consumer 1. Referring to FIG. 1, in one embodiment, the method may involve using a fitting system 100 to deliver a sequence of test audio signals 21 (FIG. 1) from an audio generator 22 housed within a handheld device 20, corresponding to multiple test sound segments 30, directly to an input 51 of a programmable hearing aid 50 in-situ (while the consumer is wearing the hearing device in the ear). In some embodiments, part or all of the sound segments 30 (also referred to herein as "digital audio files", "test audio segments" and "audio segments") are obtained from natural sound recordings such as speech and environmental sounds, with each test sound segment (S1-S8 for example) comprising a unique combination of a sound level 40 (41-48 for example) and frequency characteristics.

Figure 2:
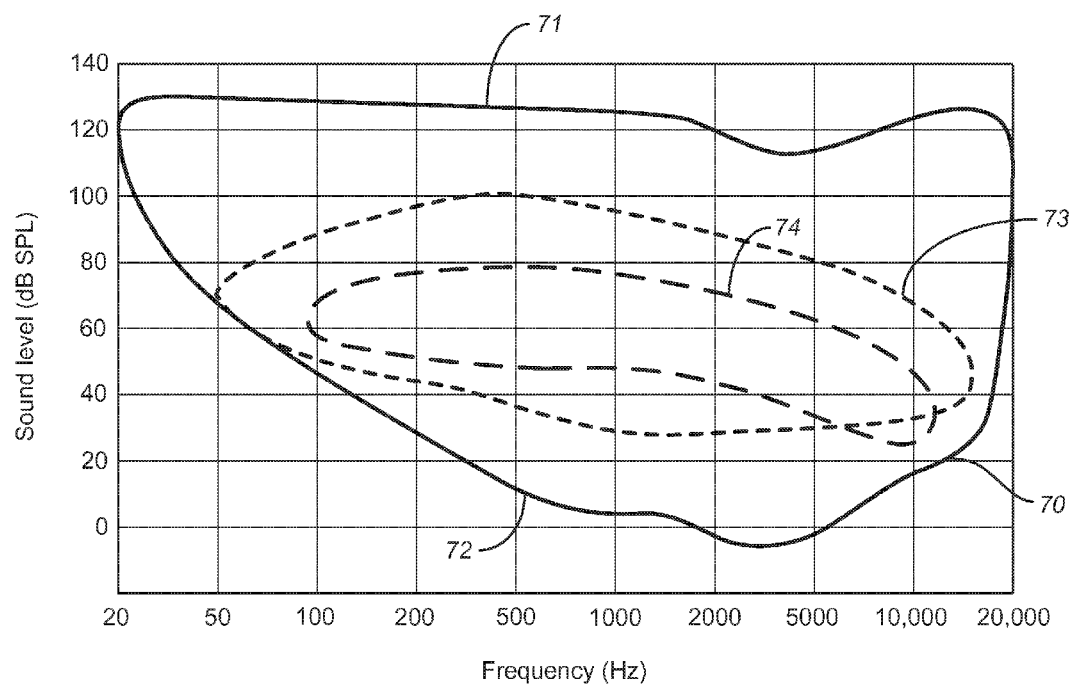
FIG. 2 is an example spectral graph depicting the human auditory range and the music and vocal ranges within the human auditory range.

FIG. 2 shows a spectral plot of the human auditory range generally spanning the frequencies between 20 to 20,000 Hz, and sound pressure between 0 dB to 130 dB SPL. Sounds naturally made, as well as certain audible man-made sounds, are considered herein as part of the auditory soundscape 70. The upper end 71 of the auditory soundscape generally refers to the threshold of pain 71, while the lower end 72 refers to the threshold of hearing. The musical range 73 and normal conversation (vocal) range 74 are also shown for reference and are generally well within the auditory soundscape 70.

Figure 3:
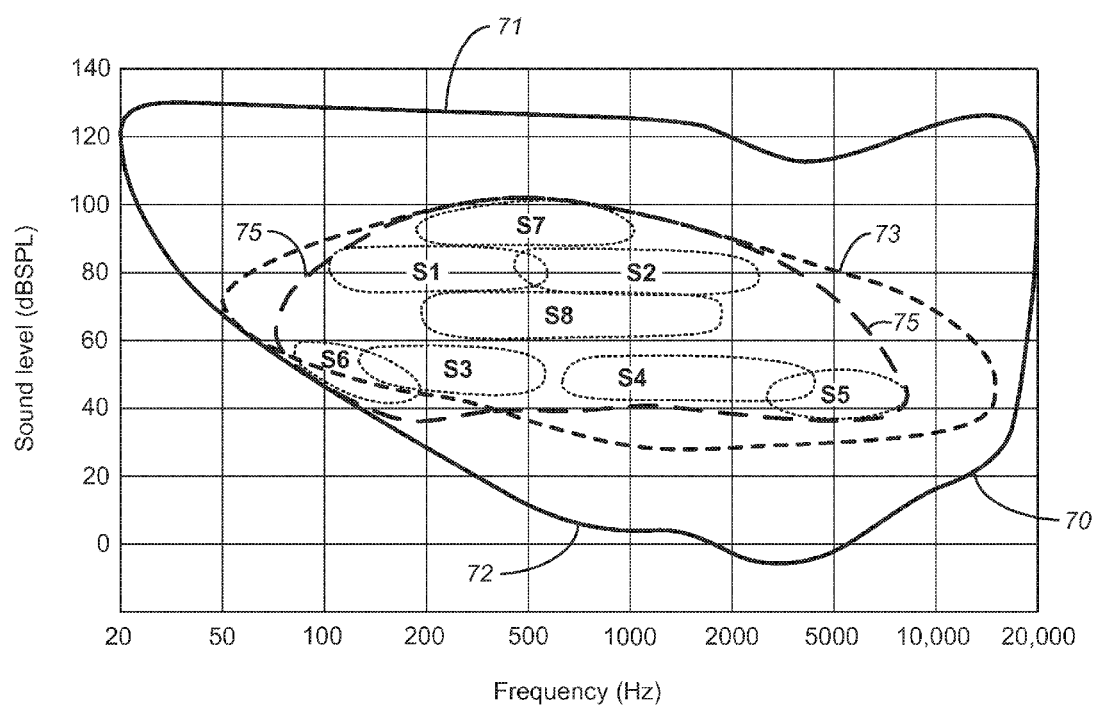
FIG. 3 is an example spectral graph of a fitting soundscape and test sound segments within.

Another aspect of the disclosure is the concept of fitting a soundscape 75 (FIG. 3) encompassing the spectrum of test sound segments 30 (S1-S8) having varied corresponding sound levels 40 and frequency characteristics for evaluating and determining effective communications in daily listening situations, and employed for conducting the fitting process according to the disclosures herein. The sound segment set 30 (FIG. 1) with spectral characteristic within the fitting soundscape 75 includes one or more relatively low level sounds (for example S3-S6) generally along the lower perimeter of the fitting soundscape 75, one or more relatively loud sounds (for example S1, S2 and S7) generally along the upper perimeter of the fitting soundscape 75, one or more relatively low frequency segments (for example S1, S3 and S6), and one or more relatively high frequency segments (for example S2, S4 and S5). The sound segments 30 within the fitting soundscape 75 are generally at suprathreshold level, with respect to threshold of hearing 72 of normal hearing as shown in FIG. 3, and preferably comprise at least two speech segments (for example any of S1-S4) and at least one environmental sound segment (for example any of S6 and S7). The sound segments 30 are generally stored in digital format, for example as digital audio files. In one embodiment, the levels of test speech sound segments are at least 20 dB above the threshold of normal hearing 72. For reference purposes, it should understood that a 0 dB HL (hearing level) represents the threshold of hearing 72 for normal hearing individuals, and "suprathreshold" refers to sound levels above the threshold of hearing 72. It is also to be understood that the sound pressure level (SPL) at the threshold of hearing 72 for normal hearing individuals varies depending on the frequency, defining a different SPL for 0 dB HL reference at each frequency.

In one embodiment, the relatively soft level speech sounds are presented within the range of 40-55 dB SPL, the relatively loud level speech sounds are presented within 75-85 dB SPL, a relatively very loud environmental sound is presented at approximately 90 dB SPL, a relatively soft background sound, such as fan noise, may be presented within 30-45 dB SPL, and broad band environmental sound, such as music or TV sounds, is presented within the range of 60-70 dB SPL for final level adjustment or balance adjustments across a pair of hearing aids during a binaural fitting.

Systems for providing realistic listening scenarios by acoustically coupling sound from a speaker to the microphone of the hearing device are known in the art. In addition to requiring an external speaker, these known fitting methods typically involve a REM incorporating calibrated probe tube microphones. To provide realistic listening scenarios, some of these systems rely on a complex setup to measure individual head related transfer function. Thus, these known systems and methods are generally limited to clinical and research settings.

Referring again to FIG. 1, one embodiment of the fitting method generally involves instructing a hearing aid consumer 1 to listen to output 55 of the in-situ programmable hearing device 50 (shown outside the ear 2 for clarity) connected to the fitting system 100. The consumer 1 is offered a user interface with controls 90 (FIG. 6) to adjust and program corresponding hearing aid parameters 80 (FIG. 6), while subjectively evaluating hearing aid output 55 in response to calibrated test audio signals, corresponding to sound segments 30 presented at suprathreshold levels, delivered to an input of the hearing device 50. In an example embodiment, test audio signals 21 are delivered directly, for example electrically to an input 51 of the hearing aid 50 by a programming cable 26, as shown in FIG. 1 (system components are not drawn to scale for clarity). Alternatively, the audio signal may be a wireless audio signal 28 (e.g. FIG. 12) delivered to a wireless input 52 (FIG. 5) of the hearing device 50. The delivery of test signals to a non-acoustic input generally eliminates the need to calibrate test sounds by REM systems or a sound level meter (SLM). In other examples (not shown), test signals representing sound segments 30 with fitting soundscape 75 may be delivered to an acoustic input (e.g. a microphone) of the hearing device 50.

Figure 4:
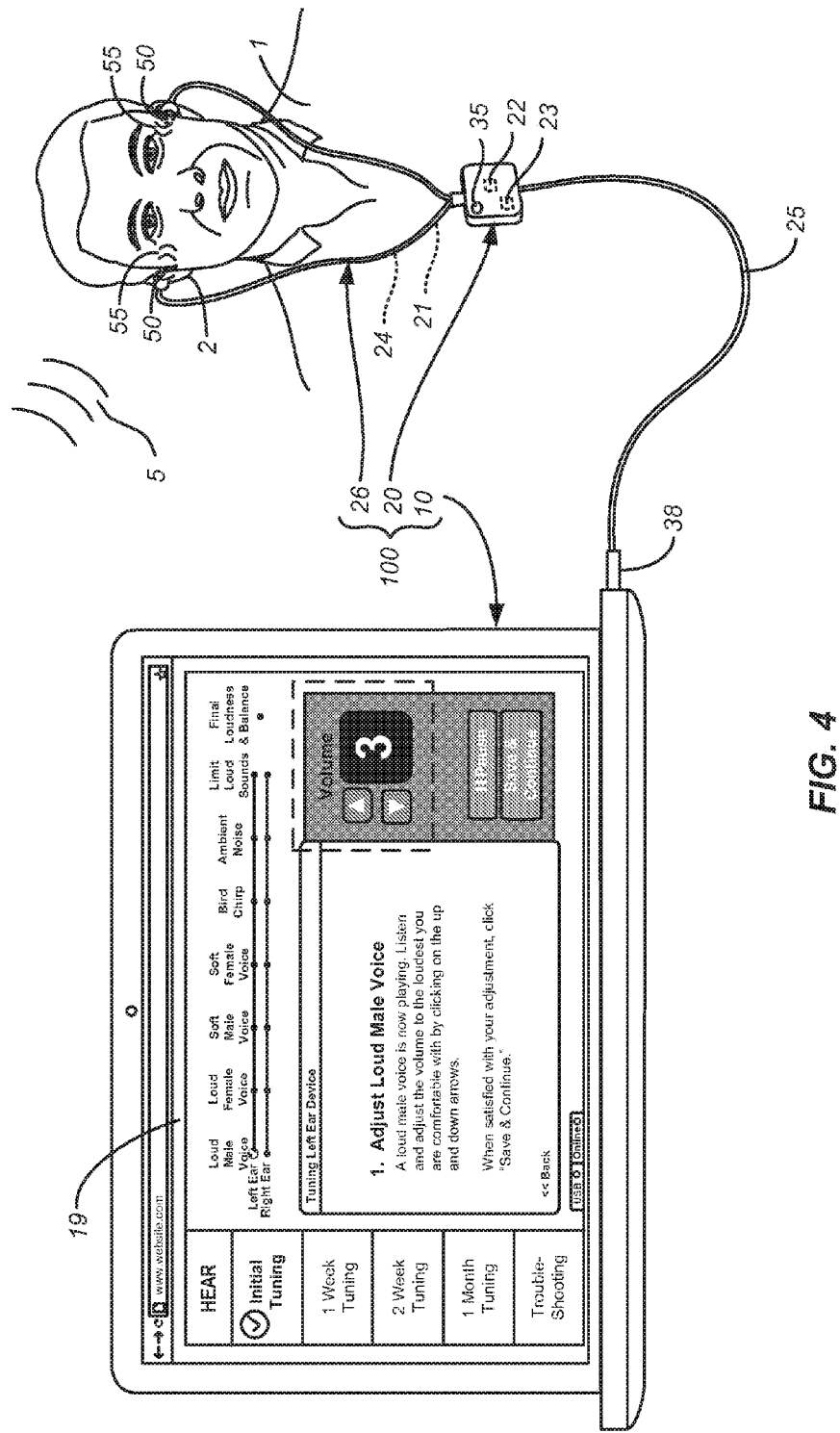
FIG. 4 is a representation of a hearing aid fitting system, including a personal computer, a handheld device for generating test audio signals and programming signals, and a programmable hearing device in-situ with direct electrical audio input for receiving test audio signals, according to one embodiment.
Figure 5:
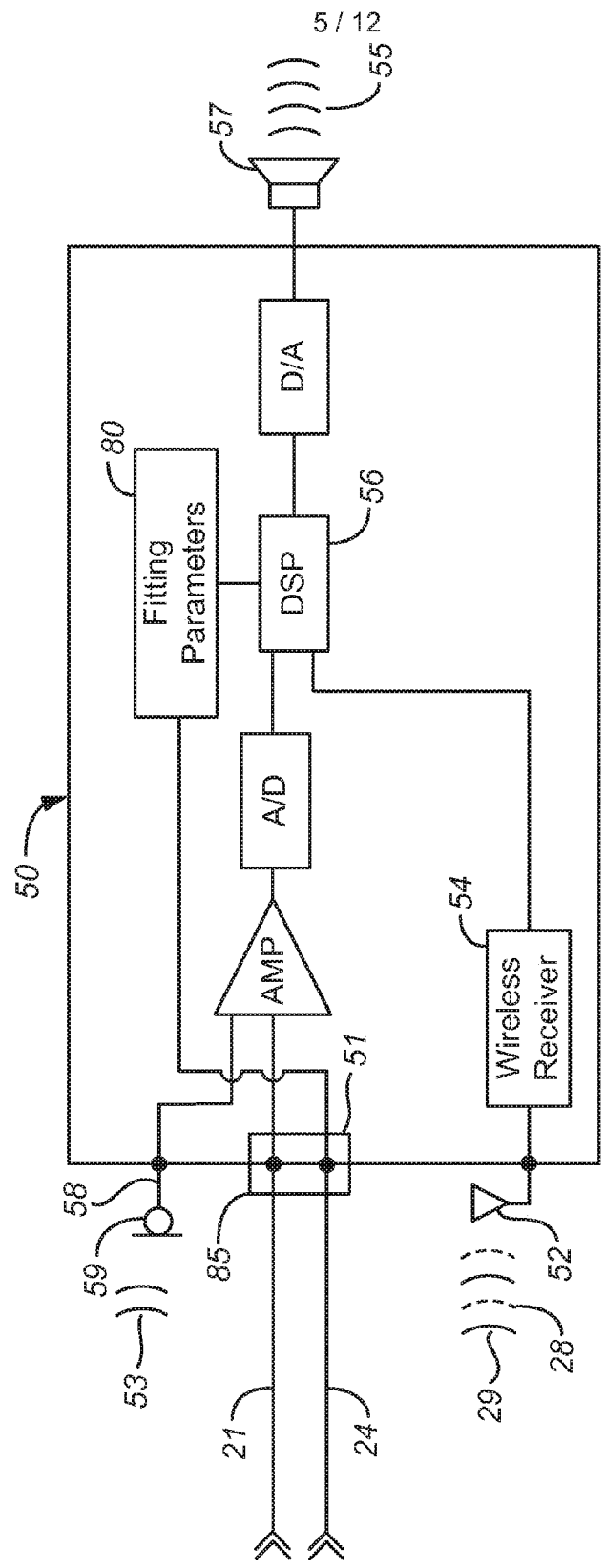
FIG. 5 is a block/circuit diagram of a programmable hearing aid, showing multiple audio input options, including a microphone (acoustic) input and non-acoustic inputs, to implement the fitting method disclosed herein, according to one embodiment.

In one embodiment, as shown in FIG. 4, the fitting system 100 includes a personal computer 10, a handheld device 20 connected to the personal computer 10, a programming cable 26, and a fitting software application for execution by the personal computer 10. The audio generator 22 housed within the handheld device 20 may be configured to convert digital audio files 30, sent as files or audio streamed by the personal computer 10, to electrical test audio signals 21, and to deliver to a non-acoustic input of a programmable hearing device 50 in-situ. For reference purposes, as shown in the block diagram of the programmable hearing aid 50 (FIG. 5), an acoustic or microphonic input generally refers to any signal associated with the microphone 59 of the hearing aid, including the electrical signal 58 generated from the microphone 59, or the test sound 53 presented thereto. Referring to FIG. 5, the example hearing aid may include a digital signal processor (DSP) 56 and a receiver (speaker) 57 for generating hearing aid output 55. The hearing aid audio inputs may be acoustic such as 53 or 58, electrical such as input 51, or alternatively a wireless input, as in input 52, in conjunction with wireless receiver 54 for receiving wireless audio signals 28 and wireless programming signal 29. Alternative hearing aid input options are shown co-existing in FIG. 5 but it should be understood that they may not all co-exist in a typical hearing aid application, or for implementing the teachings of the present disclosures.

In the electrical input embodiments of FIGS. 1 and 4, the handheld device 20 includes a programming circuit 23 (FIG. 1) configured to generate and deliver programming signals to the programmable hearing device 50 in-situ. The handheld device 20 in one embodiment is provided with USB connectivity 25 for interfacing with abroad range of general purpose computing devices, including personal computers, smartphones and tablet computers. The USB connectivity may include a USB connector 38. The programming circuit 23 may comprise I$^2$C (inter-integrated circuit) to implement I$^2$C communications as known in the art of electronics and programmable hearing aids. In some embodiments, consumer controls 90 (FIG. 6) for adjusting hearing aid parameters 80 are offered by the fitting software application to the consumer 1 for subjective assessment and selection generally in lay terms, such as loudness, audibility, clarity, etc., rather than technical terms and controls conventionally offered to hearing professionals such as gain, compression ratio, expansion ratio, etc.

To mitigate the effects of room noise in certain room environments, a microphone 35 may be incorporated, such as within the handheld device 30, to generally sense sound 5 present in the vicinity of the consumer 1. The hearing aid fitting process may then be adjusted according to the noise condition. For example, by delaying the presentation of test stimuli during a noise burst in the room, or by halting the test process in the presence of excessive noise.

The computing system employed by the fitting system 100 generally includes one or more processing unit(s), which may be implemented using one or more processors, and memory loaded or encoded with executable instructions for executing a fitting application to adjust fitting parameters 80. The executable instructions for fitting parameter adjustment, when executed, may cause the processing unit(s) to perform computations and programming of fitting parameter adjustments described herein. The handheld fitting device 20 may also include a processing unit such as a microcontroller, memory with executable instructions for delivery of test audio signals and programming signals to the programmable hearing device.

Figure 12:
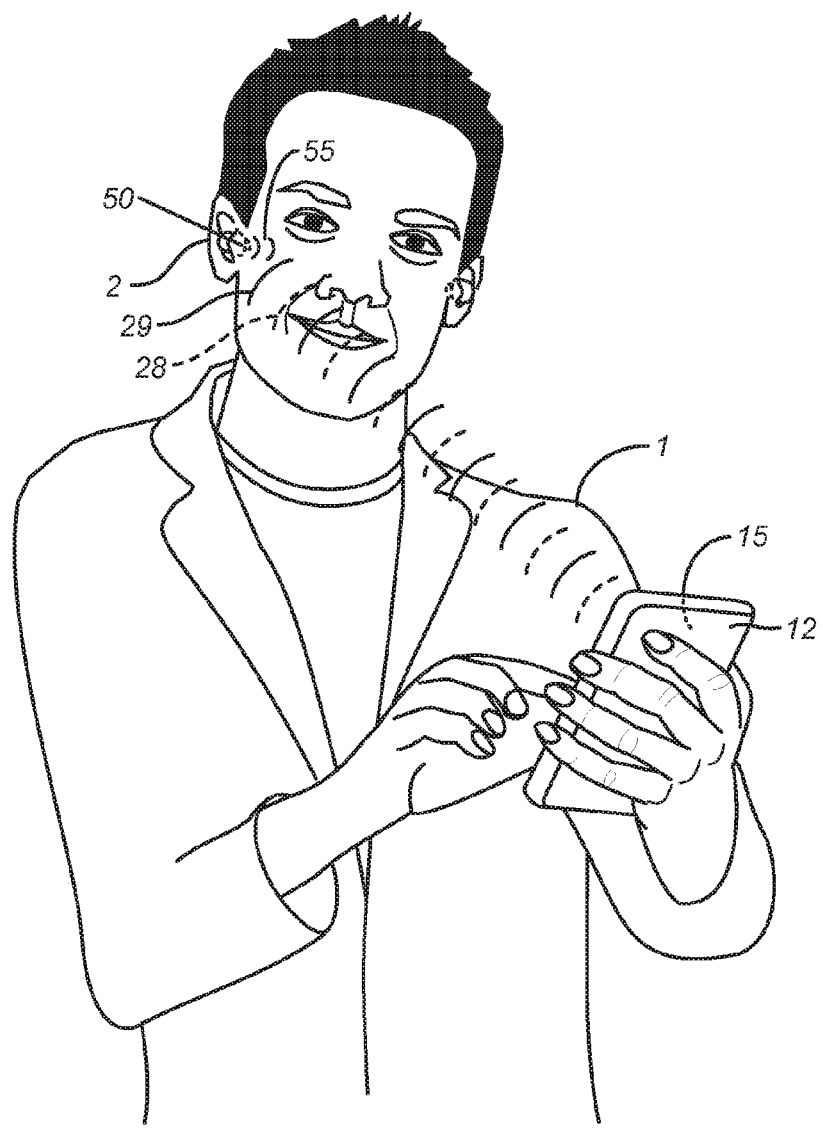
FIG. 12 is a perspective view of a wireless implementation of the hearing aid fitting system using a smartphone executing a hearing aid fitting application, wherein the system is configured to transmit a wireless programming signal and a wireless test audio signal to the programmable hearing device in-situ, according to one embodiment.

Using various embodiments of the fitting system 100, consumers may interactively develop their own "prescriptions" and program into their programmable hearing devices, relying on the subjective assessment of hearing aid output 55 and without dealing with prescriptive formulae or specialized fitting instruments or relying on professionals and clinical settings. The test audio signals 21 are automatically generated by the fitting system and presented directly to an input of the hearing device at a predetermined level, for example electrically to an electrical input 51, or wirelessly by a wireless audio signal 28 (FIGS. 5 and 12). The predetermined level of audio signals eliminates calibration processes associated with delivering test sound 53 to the microphonic input of hearing aids. Similarly, the programming signal 24 may be configured to adjust hearing aid parameters 80 by the fitting system 100. The programming signal may be presented electrically to electrical input 51 by a fitting connector 85 (FIG. 1) associated with the programming cable 26, or wirelessly by transmitting the programming signal 29 to the wireless input 52 (FIG. 5). In the example of FIG. 1, the fitting connector 85 is electromechanically connected to a main module of a modular canal hearing device to deliver audio signals 21 and programming signals 24 to electrical input 51 of the modular canal heating device 50. In an alternate embodiment (not shown), acoustic test signals may be presented to the microphone of the hearing device 50, for example, from a headphone worn with its speaker positioned in proximity to the hearing device 50 in-situ, for example a canal hearing device worn in the ear canal.

The fitting system 100 may allow the consumer 1 to manipulate hearing aid parameters 80 indirectly by user controls 90, based on the subjective response to hearing aid output 55 presented in the ear 2. The process of presenting audio signals and programming according to the subjective assessment of the consumer is repeated for each test audio segment until all corresponding fitting parameters 80 are adjusted according to the instructions provided to the consumer for each sound segment. In the preferred embodiments, the test audio segments 30 are selected with minimal overlap in the combination of level 40 and frequency characteristics, thus minimizing the overlap in parameter optimization and expediting the fitting process for administration by a non-expert user, including for self-administration.

The fitting system 100 and method allows the dispensing of a hearing aid and administering the fitting process at a non-clinical environment, such as in a home or an office. The hearing aid may be delivered to the consumer's home, by mail for example. This "home fitting" aspect substantially reduces the cost of hearing aid acquisition and eliminates hassles and inconvenience associated with multiple visits to professional settings. In one embodiment, the fitting process may be conducted online, with a fitting software application hosted by a remote server for execution by a personal computer 10 connected online to the server.

Figure 7:
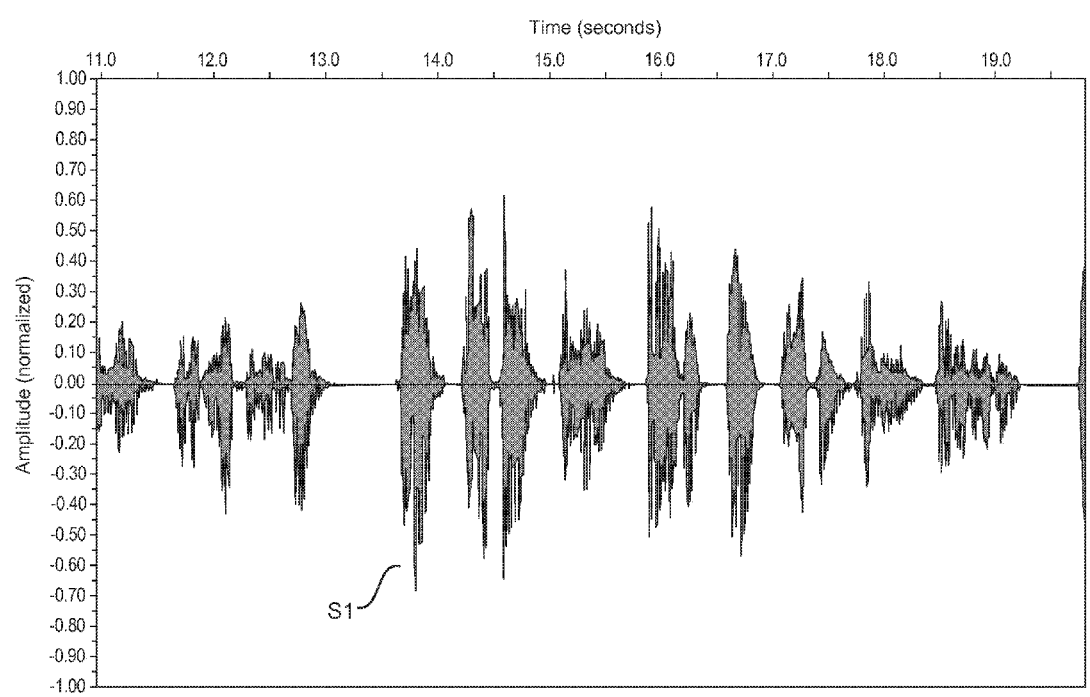
FIG. 7 is a time domain graph of an example loud male speech segment for evaluating and adjusting loudness control, corresponding to a high-level gain parameter in a low-frequency band of hearing aid signal processing.
Figure 8:
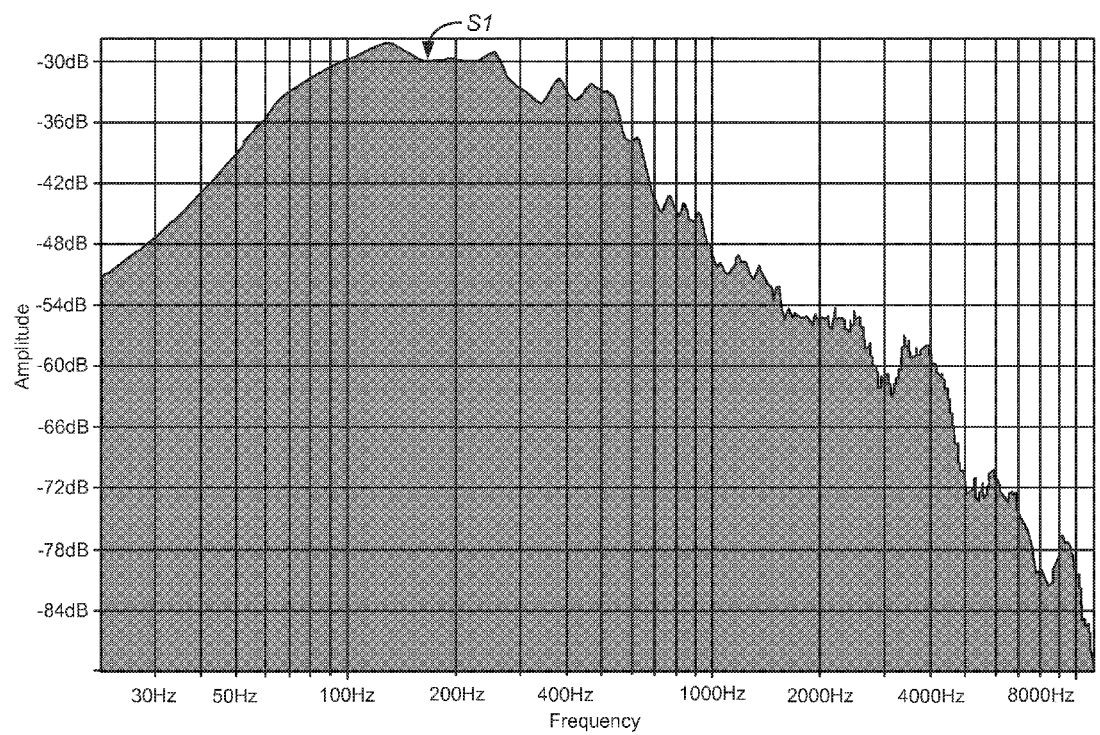
FIG. 8 is a frequency spectrum graph of the example male speech segment of FIG. 7, illustrating relatively dominant low frequency characteristics.

Another aspect of the present disclosure is to present real-life scenarios with a set of audio segments 30 selected specifically to expose the range of hearing aid parameters 80 within a hearing device 50 for their adjustment by a non-expert user using subjective assessment without clinical instrumentation. Natural sound recordings may be filtered by an audio processor application, for example Audacity® for Windows, to enhance and tailor the spectral characteristics of a natural sound recording to a corresponding set of fitting parameters. For example, a loud male speech segment S1 may be presented at a signal level corresponding to sound pressure level 41 of approximately 80 dB SPL. A calibration constant associated with sound level calibration for each sound segment is stored in the memory of the fitting system 100. In some embodiments, relatively loud speech signals may be presented in the range of 75-85 dB SPL. FIG. 7 shows a time domain plot of an example loud male speech segment S1 employed to allow a consumer 1 to adjust a high-level gain parameter 81 (FIG. 6) in the low frequency band range, referred to herein as B1. The original male speech recording may be filtered by the aforementioned audio processor application to enhance the low frequency spectral characteristics as shown in FIG. 8.

Figure 9:
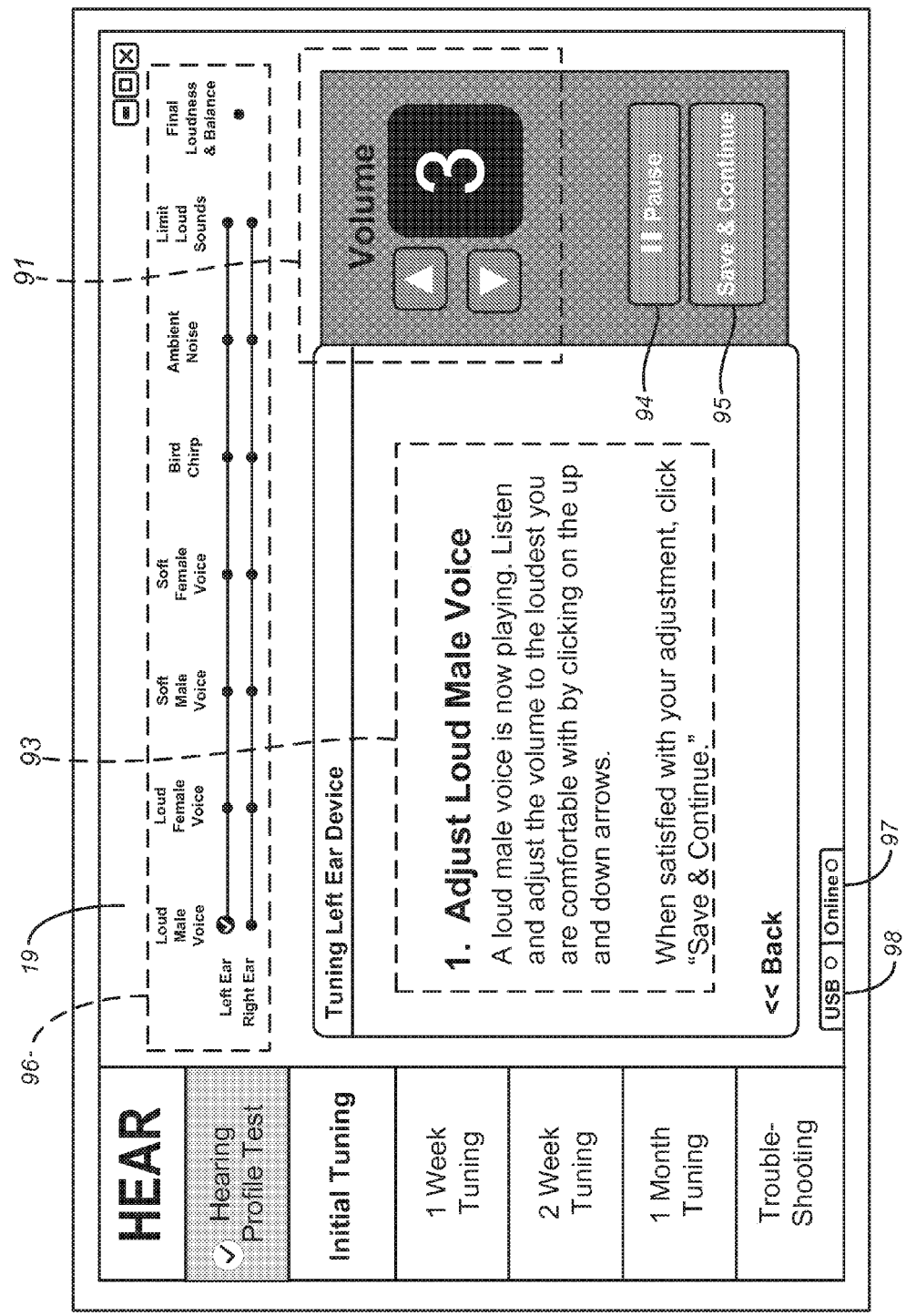
FIG. 9 is a representation of a user interface WI) to adjust loudness and corresponding high-level gain in the low frequency band of signal processing of a hearing aid connected to the fitting system, during a presentation of the loud male speech of FIGS. 7 and 8, wherein the UI also shows instructions and indicators for a non-expert user, according to one embodiment.

FIG. 9 shows an example user interface (UI) 19 for a fitting software application with loudness (Volume) control 91 provided to the consumer 1 to adjust the high-level gain parameter 81 of the hearing device 50 in B1. The UI 19 shows UI elements including user instructions 93, pause control 94, save control 95, fitting process status 96, online connection status 97, and handheld device 20 USB connection status 98. In some examples, the subjective assessment of "Volume" (loudness) of hearing aid output 55 with "Loud Male Voice" specifies gain fitting parameter 81 of the hearing device 50 corresponding to loudness in the low frequency band. The consumer 1 may use the volume control 91 to increase the loudness of hearing aid output 55, using an up arrow, based on a subjective assessment that hearing aid output 55 was not sufficiently loud. In another example, the consumer 1 may use a down arrow of volume control 91 to decrease the loudness of hearing aid output 55 using, based on a subjective assessment that the hearing aid output 55 was uncomfortably loud. The subjective assessment of the consumer 1 is generally correlated to an adjustment of one or more fitting parameters 80, which may be interactively adjusted by presenting test audio signals 21 at predetermined levels and transmitting programming signals 24 to the hearing device 50, as described by the example process above. The computation for adjusting fitting parameters 80 may be performed by a processor within the fitting system 100, for example a microprocessor within the personal computer 10 or a remote server, or a microcontroller within the fitting device 20. Other examples, shown in the process status 96 of user interface 19 of FIG. 9, relate to other subjective aspects of audibility such as threshold of hearing audibility and clarity for "Soft Female Voice", annoyance of "Ambient Noise", and audibility of ultra high-frequency sound represented by a "Bird Chirp". Fitting parameters 80 associated with the subjective aspects of audibility may be adjusted based on a selection by the consumer 1 through a user interface, similar to the adjustment of gain fitting parameters 81 associated with loudness perception described above.

In a preferred embodiment, the fitting software application is browser-based as shown in FIG. 9 and operates in conjunction with a client application that allows access and control of the handheld device 20. The personal computer 10 and the handheld device 20 include memory (not shown) to store components of fitting software, such digital audio files representing test sound segments 30, calibration constants, test results, user information, etc.

Figure 6:
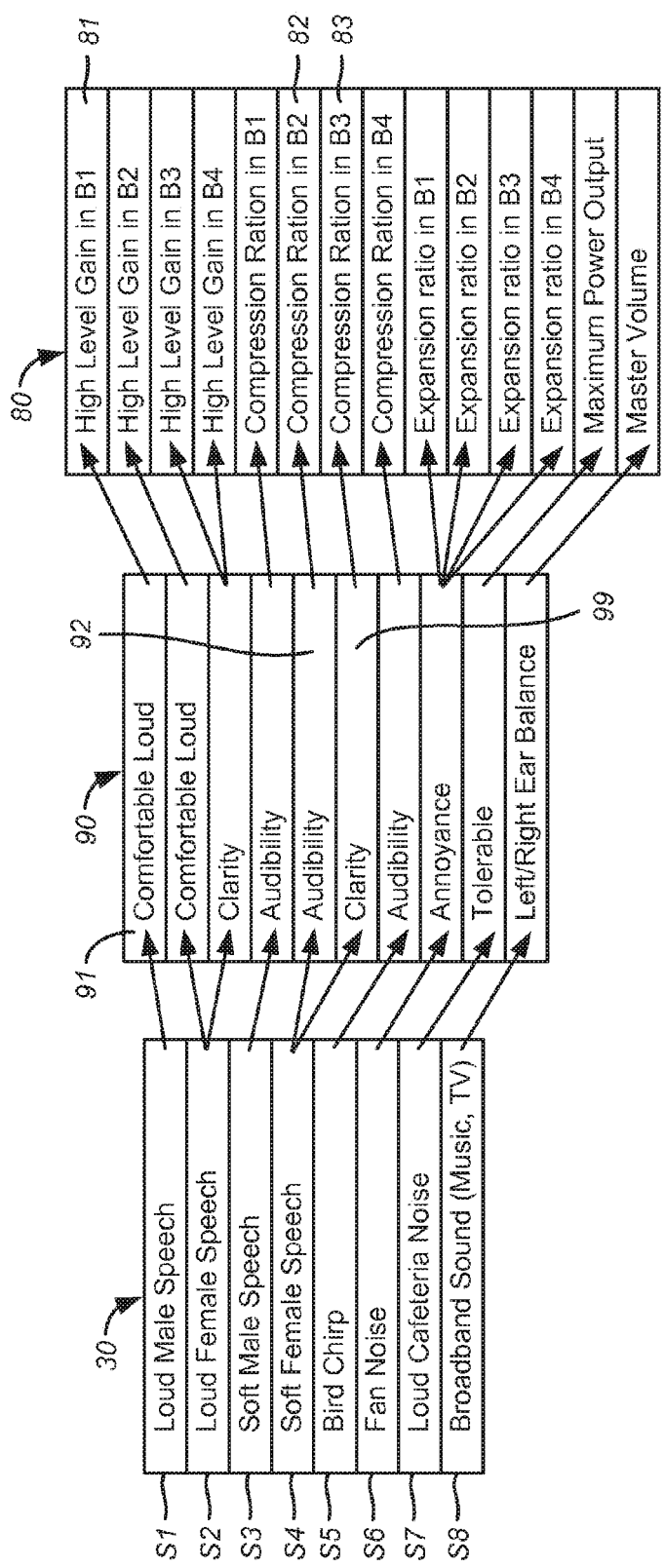
FIG. 6 depicts multiple test sound segments and their assignment to corresponding consumer controls and fitting parameters of a programmable hearing aid, according to one embodiment.
Figure 10:
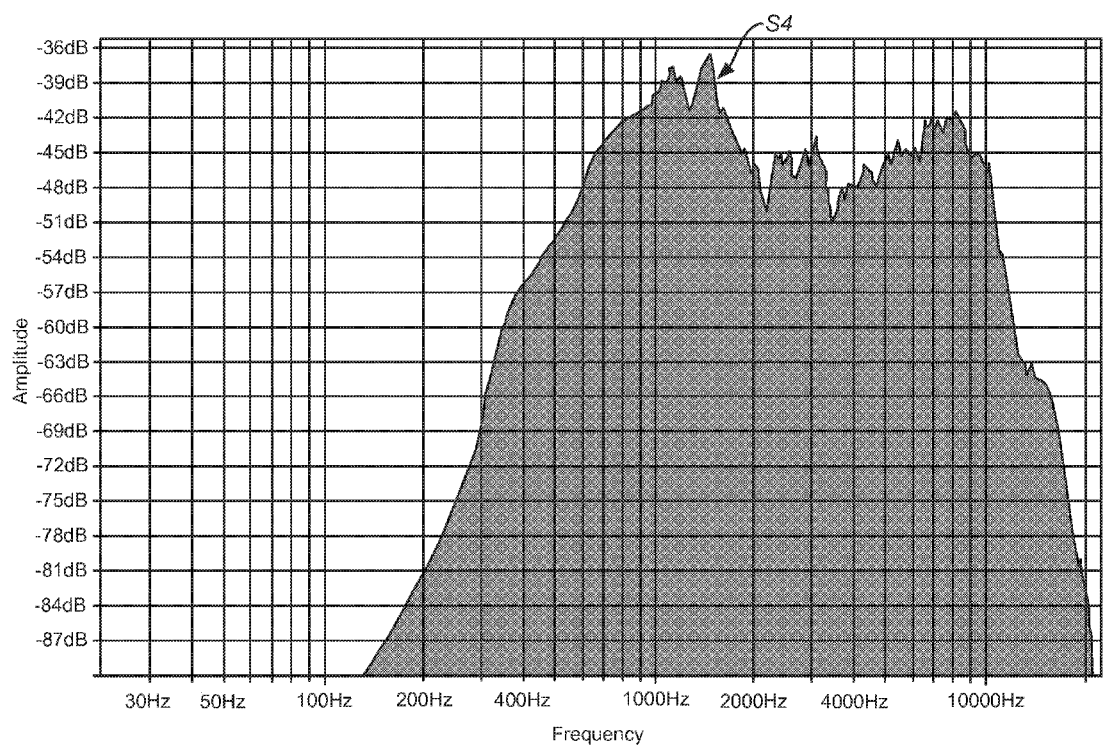
FIG. 10 is a frequency spectrum graph of an example soft female speech test segment illustrating relatively dominant mid and high frequency characteristics.

FIG. 10 shows a spectral plot of an example soft female speech segment S4 employed to adjust user controls for audibility 92 and clarity 99, corresponding respectively to compression ratio 82 in the mid frequency band B2 and compression ratio 83 in the high frequency band B3, as shown in FIG. 6. The original female speech recording was also filtered by the aforementioned audio processor application to reduce low frequency content and enhance spectral characteristics in the mid and high bands as shown in FIG. 10. In various embodiments, a single sound segment (S1-S8) may correspond to a single or multiple user control 90, and similarly a single user control 90 may correspond to a single or multiple fitting parameters 80, as shown in FIG. 6.

Figure 11:
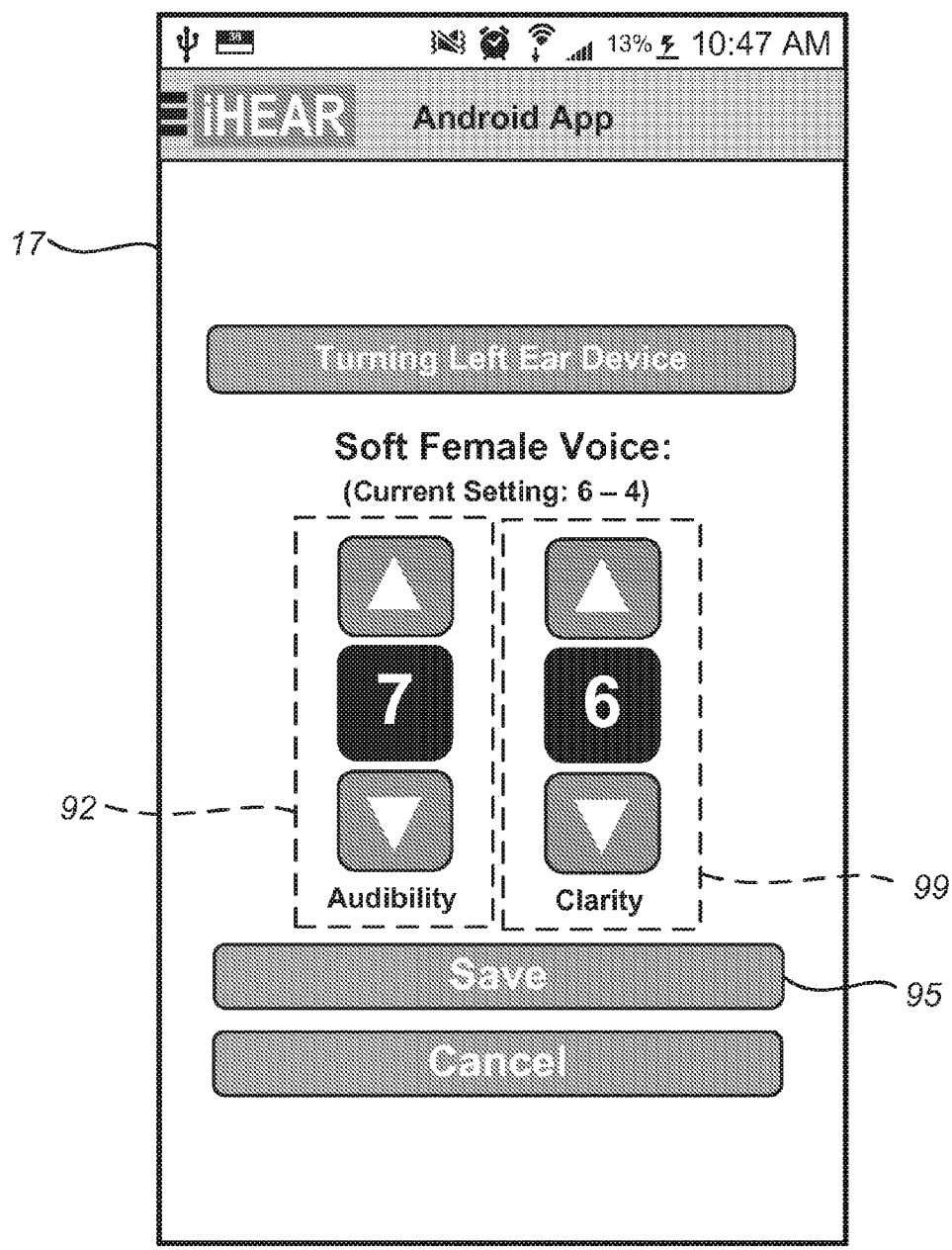
FIG. 11 is a representation of a user interface (UI) for a smartphone to adjust multiple controls corresponding to multiple fitting parameters of a hearing aid during the presentation of the soft female speech of FIG. 10, wherein the UI shows audibility control, clarity control and indicators, according to one embodiment.

FIG. 11 shows an example user interface (III) 17 for a smartphone fitting application to adjust fitting parameters 82 and 83, associated with soft female speech. UI 17 may include UI elements such as audibility control 92, clarity control 99, and save function control 95. Similarly, the user 1 may be instructed to listen to a soft female sound, and adjust controls 92 and 99 on the touch screen 15 (FIG. 12) of the smartphone 12, according to the listening experience from the in-situ hearing aid output 55, with a presentation of soft female speech to the hearing aid input. In various embodiments, other fitting parameters 80 may be adjusted in a substantially similar manner using the user's subjective response to hearing aid output in-situ. FIG. 12 shows a wireless embodiment of the fitting system 100, whereby wireless audio signals 28 and wireless programming signals 29 are wirelessly transmitted from the smartphone to implement the aforementioned teachings of the fitting process in conjunction with a wireless embodiment of the programmable hearing device 50. The fitting system and interactive methods disclosed herein enable self-fitting for a consumer 1 with minimal computer skills, or by a non-expert person assisting the consumer 1.

Although examples of the invention have been described herein, variations and modifications of this exemplary embodiment and method may be made without departing from the true spirit and scope of the invention. Thus, the above-described embodiments of the invention should not be viewed as exhaustive or as limiting the invention to the precise configurations or techniques disclosed. Rather, it is intended that the invention shall be limited only by the appended claims and the rules and principles of applicable law.

What is claimed is:

1. A method of hearing device fitting for a consumer, the method comprising:
   generating a suprathreshold output from a programmable hearing device in-situ, wherein the output is based, at least in part, on fitting parameters programmed into the programmable hearing device; and
   making adjustments to a plurality of the fitting parameters based, at least in part, on the consumer's assessment of the output, wherein the adjustments comprise a first adjustment made to one or more first fitting parameters corresponding to a relatively loud level sound segment and a second adjustment made to one or more second fitting parameters corresponding to a relatively soft level sound segment.

2. The method of claim 1, wherein the output comprises multiple natural sounds.

3. The method claim 2, wherein the natural sounds are selected from the group consisting of male speech, female speech, chirp, and background noise.

4. The method of claim 1, wherein the fitting parameters comprise any of a loud level gain, a soft level gain, a compression ratio, a maximum power output, and an expansion ratio.

5. A method of adjusting a hearing device for a consumer, the method comprising:
   generating a suprathreshold output from a programmable hearing device in-situ, wherein the output is based, at least in part, on programmable parameters programmed into the programmable hearing device; and
   making adjustments to a plurality of the programmable parameters based, at least in part, on the consumer's assessment of the output, wherein the adjustments comprise a first adjustment made to one or more first programmable parameters corresponding to a relatively loud level sound segment and a second adjustment made to one or more second programmable parameters corresponding to a relatively soft level sound segment.

6. A programmable hearing device comprising:
a speaker configured to generate a suprathreshold output based, at least in part, on programmable parameters of the programmable hearing device; and
a processing unit configured to make adjustments to the programmable parameters in-situ based on a consumer's assessment of the output, wherein the adjustments comprise a first adjustment made to one or more programmable parameters corresponding to a relatively loud level sound segment and a second adjustment made to one or more programmable parameters corresponding to a relatively soft level sound segment.

7. The programmable hearing device of claim 6, further comprising a wireless interface configured to receive one or more test audio signals from any of a personal computer, a smartphone, or a tablet.

8. The programmable hearing device of claim 6, wherein the output comprises at least two sound segments representing natural sound, wherein the sound segments are substantially non-overlapping in a combination of sound level and frequency characteristics.

* * * * *